US011458112B2

(12) United States Patent
Thor et al.

(10) Patent No.: US 11,458,112 B2
(45) Date of Patent: Oct. 4, 2022

(54) COMPOSITIONS AND METHODS FOR INDUCING DEFECATION (71) Applicant: Dignify Therapeutics, LLC, Research Triangle Park, NC (US)

(72) Inventors: Karl Bruce Thor, Cary, NC (US); Lesley Marson, Chapel Hill, NC (US)

(73) Assignee: DIGNIFY THERAPEUTICS, LLC, Research Triangle Park, NC (US)

( * ) Notice: Subject to any disclaimer, the term of this patent is extended or adjusted under 35 U.S.C. 154(b) by 0 days.

(21) Appl. No.: 16/775,538

(22) Filed: Jan. 29, 2020

(65) Prior Publication Data

US 2021/0015771 A1    Jan. 21, 2021

Related U.S. Application Data (63) Continuation of application No. PCT/US2019/042320, filed on Jul. 18, 2019.

(51) Int. Cl.
*A61P 1/14* (2006.01)
*A61K 31/165* (2006.01)
*A61P 1/10* (2006.01)
*A61K 9/02* (2006.01)
*A61K 9/00* (2006.01)

(52) U.S. Cl.
CPC .......... *A61K 31/165* (2013.01); *A61K 9/0031* (2013.01); *A61K 9/02* (2013.01); *A61P 1/10* (2018.01)

(58) Field of Classification Search
CPC .................................... A61P 1/10; A61P 1/14
See application file for complete search history.

(56) References Cited

U.S. PATENT DOCUMENTS

| 10,086,034 B2 | 10/2018 | Thor et al. | |
| 2002/0071872 A1* | 6/2002 | McNally | A61K 31/4402 424/490 |
| 2006/0240125 A1* | 10/2006 | Astrup | A61K 2300/00 424/682 |
| 2010/0159000 A1* | 6/2010 | Lundeen, Sr. | A61K 31/4439 514/217 |

OTHER PUBLICATIONS

Hayashi et al (Intracolonic capsaicin stimulates colonic motility and defecation in conscious dogs, Presentation at 21st International Symposium on Neurogastroenterology and Motility, Surgery) (Year: 2010).*
Hayashi et al. (Intracolonic capsaicin stimulates colonic motility and defecation in conscious dogs; Surgery, 2010, ppg 789-797) (Year: 2010).*
Sander JM van Wanrooji et al (Sensitivity Testing in Irritable Bowel Syndrome With Rectal Capsaicin Stimulations: Role of TRPV1 Upregulation and Sensitization in Visceral Hypersensitivity?, Am J Gastroenterol 2014; 109:99-109) (Year: 2014).*
Kikuchi et al. (Role of the intraluminal contents and the continuity of intrinsic neurons in intracolonic capsaicin-induced contraction and defecation in dogs; Surg Today 44:152-159, 2014) (Year: 2014).*
Horii, Kazuhiro, et al., "Sexually dimorphic response of colorectal motility to noxious stimuli in the colorectum in rats", The Journal of Physiology, 599.5, Mar. 2021, 17 pages.
Naitou, Kiyotada, et al., "Descending monoaminergic pathways projecting to the spinal defecation center enhance colorectal motility in rats", Am J Physiol Gastrointest Liver Physiol, 315, Aug. 2, 2018, 7 pages.
ISA/US; International Search Report and Written Opinion for International Patent Application No. PCT/US 19/42320 dated Sep. 24, 2019, 8 pages.
Callaghan, B., et al., "Neural pathways for colorectal control, relevance to spinal cord injury and treatment: a narrative review" ISCOS, Springer Nature, Nov. 16, 2017, 8 pages.
Fattori, V., et al., "Capsaicin: Current Understanding of Its Mechanisms and Therapy of Pain and Other Pre-Clinical and Clinical Use", MDPI, Molecules, 2016, vol. 21, No. 844, pp. 1-33.
Hayashi, K., et al., "Intracolonic capsaicin stimulates colonic motility and defecation in conscious dogs", Surgery, vol. 147, No. 6, pp. 789-797.
Jannin, V., et al., "Rectal route in the 21st Century to treat children", Elsevier, Advanced Delivery Drug Reviews, vol. 73, 2014, pp. 34-49.
Kikuchi, D., et al., "Role of the intraluminal contents and the continuity of intrinsic neurons in intracolonic capsaicin-induced contraction and defecation in dogs", Springer, Surgery Today, vol. 44, 2014, pp. 152-159.
Macdonagh, R., et al., "Anorectal function in patients with complete supraconal spinal cord lesions", Gut, vol. 33, 1992, pp. 1532-1538.
Matsumoto, K., et al., "Localization of TRPV1 and contractile effect of capsaicin in mouse large intestine: high abundance and sensitivity in rectum and distal colon", American Journal of Gastrointestinal and Liver Physiology, vol. 387, Jun. 4, 2009, pp. G348-G360.
Reyes-Escogido, et al., "Chemical and Pharmacological Aspects of Capsaicin", MDPI, Molecules, vol. 16, 2011, pp. 1253-1270.
Shafik, A., et al., "Role of the sigmoid colon in the defecation mechanism with evidence of sigmoido-anal inhibitory and anosigmoid excitatory reflex", Frontiers in Bioscience, vol. 6, Oct. 1, 2001, b25-b29.

(Continued)

Primary Examiner — Micah Paul Young
(74) Attorney, Agent, or Firm — NK Patent Law (57) ABSTRACT Methods, pharmaceutical formulations, and kits are provided for using capsaicin to effectuate voluntary defecation in mammals who cannot defecate without external invasion of the bowel or those who defecate involuntarily (i.e., those having fecal incontinence). The pharmaceutical formulations and kits can also be useful for inducing defecation in mammals that do not have defecation dysfunction such as, for example, in a person who is unconscious and may defecate unconsciously or in a pet at a convenient location at a specific time. The methods and compositions provide patients with defecation dysfunction control over when and where they defecate.

16 Claims, 4 Drawing Sheets (56) References Cited

OTHER PUBLICATIONS

Shafik, A., "A study of the effect of distension of the rectosigmoid junction on the rectum and anal canal with evidence of a rectosigmoid-rectal reflex" Journal of Surgical Research, vol. 82, No. 1, Mar. 1999, pp. 73-77.

Shafik, A., "Recto-colic reflex: role in the defecation mechanism", International Surgery, vol. 81,1996, pp. 292-294.

National Spinal Cord Injury Statistical Center, "Spinal Cord Injury Facts and Figures at a Glance: 2019 SCI Data Sheet", 2 pages.

Van Wanrooij, et al., "Sensitivity Testing in Irritable Bowel Syndrome With Rectal Capsaicin Stimulations: Role of TRPV1 Upregulation and Sensitization in Visceral Hypersensitivity?", American Journal of Gastroenterology, vol. 109, Nov. 5, 2013, pp. 99-109.

WIPO; International Preliminary Report on Patentability for International Patent Application No. PCT/US2019/042320 dated Jan. 27, 2022, 7 pages.

\* cited by examiner

COMPOSITIONS AND METHODS FOR INDUCING DEFECATION

CROSS-REFERENCE TO RELATED APPLICATION

This application is a continuation of International Patent Application No. PCT/US19/42320, filed Jul. 18, 2019, the entire content of which is incorporated herein by reference.

TECHNICAL FIELD

The presently disclosed subject matter relates to methods of using capsaicin for inducing defecation.

BACKGROUND

Figure 1:
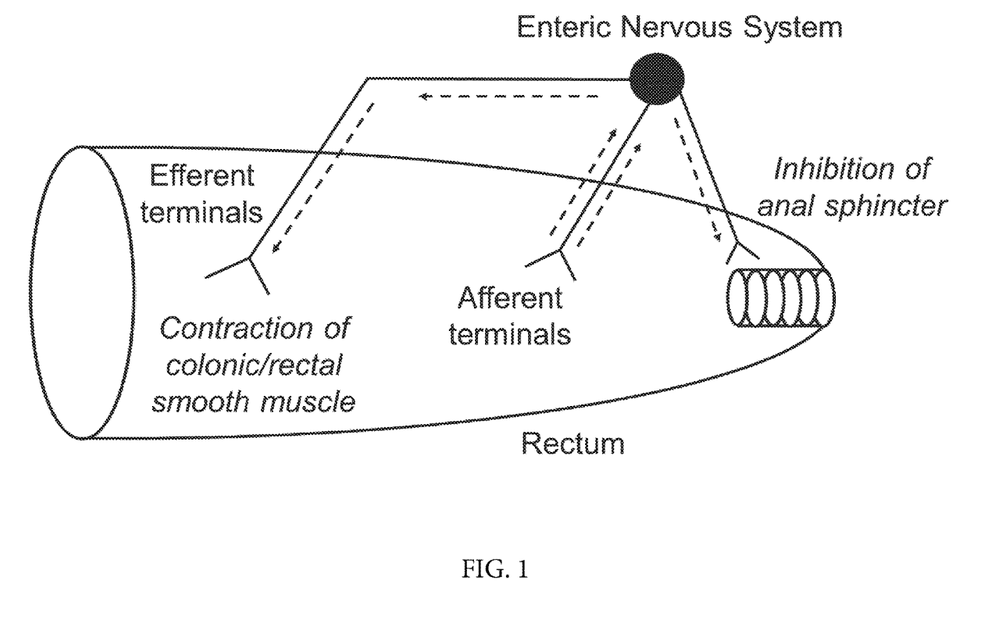
FIG. 1 is a schematic diagram showing the rectoanal inhibitory reflex underlying defecation.

Feces are formed in the large intestine and temporarily stored in the rectum. In healthy individuals, as feces fill and expand the rectum, activation of peripheral and spinal defecation reflexes produce peristaltic contractions of the descending and sigmoid colon. As schematically illustrated in FIG. 1, subsequent rectal contractions are accompanied by coordinated relaxation of the internal anal sphincter (i.e., the rectoanal inhibitory reflex) and external anal sphincter (i.e., spinal recto-rhabdosphincter inhibitory reflex) to allow passage of stool through the anal canal (MacDonagh, Sun et al. 1992, Shafik 1996, Shafik 1999, Shafik, El-Sibai et al. 2001, Callaghan, Furness et al. 2018). As can be seen, defecation is initiated by stimulus activation of afferent terminals in the rectal wall that, in turn, produces simultaneous rectal contraction and inhibition/relaxation of the anal sphincter (i.e. the rectoanal inhibitory reflex).

The inability to voluntarily eliminate feces (i.e. defecation dysfunction) is a life-threatening condition. The current standard of care for defecation dysfunction includes digital extraction of feces from the rectum in combination with laxatives, enemas and a diet conducive to stool passage.

Individuals with defecation dysfunction may also experience episodes of incontinence, whereby the large volume of feces in the rectum are subject to acute increases in intraluminal pressure that force a proportion of the feces in the rectum past the anal sphincters without completely emptying the distal colon.

Defecation dysfunction is extremely prevalent in patients with spinal cord injury, spina bifida, multiple sclerosis, and other conditions involving spinal cord pathology. Defecation dysfunction is also prevalent in subjects with diabetic gastroenteropathy. Defecation dysfunction is also seen in various elderly subjects and is prevalent among the institutionalized elderly.

Spinal cord injury (SCI) is the most common injury that profoundly affects defecation and usually results from traffic accidents, sports injuries, but also from infections, vascular disorders, cancers, congenital malformations, polio, tuberculosis, etc. It is estimated that the annual incidence of SCI, not including those who die at the scene of the accident, is approximately 54 cases per million population in the U.S. or approximately 17,730 new cases each year. The number of people in the United States in 2019 who have SCI has been estimated to be approximately 291,000 persons, with a range from 249,000 to 363,000 persons (National Spinal Cord Injury Statistical Center, Facts and Figures at a Glance. Birmingham, Ala.: University of Alabama at Birmingham, 2019.)

Injury to the spinal cord and/or brain can lead to inability to voluntarily defecate. Thus, the vast majority of individuals with SCI must invest considerable time in a "bowel program," using digital rectal stimulation and manual extraction of stool, applied by themselves (56%) or by their caregivers (44%). The defecation reflex is triggered by inserting the fingers into the rectum and stroking the epithelial lining. This stroking imitates and amplifies the physiological stimulation of rectal mechanoreceptors when stool passes into the rectum and induces action potentials in the terminals of intrinsic and extrinsic primary afferent mechanoreceptors located in the mucosal layer of the rectum. Mechanoreceptor stimulation activates peripheral and spinal defecation reflexes and initiates secretion of mucus and electrolytes from enterocytes, which facilitates the passage of stool.

Intrarectal suppository "stimulants" (e.g., bisacodyl or glycerin) have been used to facilitate defecation. These stimulants permeabilize the mucosal barrier of the rectum, allowing irritative substances in the feces to activate nociceptive afferent nerve terminals in the submucosa. Afferent activation signals the GI tract to secrete mucus and electrolytes, contract the rectum, relax the anal sphincter, and eliminate the irritating substances. However, these agents can require 30 min to initiate defecation, and they can continue to stimulate defecation for hours after administration, which raises concern about post-defecation fecal incontinence. They also cannot be used every day due to long-term damage of the lining of the GI tract and tolerance to the stimulant effects.

Bowel programs consume anywhere from 30 minutes-2 hours in 56% of people with SCI, many of whom must perform their bowel program daily (42%) or every other day (23%). In addition to manual extraction of feces, large volume (1 L) warm water enemas are used that require sitting on the toilet for 30 minutes to an hour while the water and fecal contents are expelled. In some cases, an irritative "stimulant laxative" is administered intra-rectally, although effects may last hours longer than necessary and cannot be administered on a regular basis. These methods can be degrading to the self-esteem of patients and can be personally demoralizing, altering social relationships, leading to depression, anger, poor self-image, embarrassment, frustration, etc.

If the distal colon is not emptied routinely, stool in the rectum can trigger colorectal contractions, leading to involuntary activation of the defecation reflex and fecal incontinence. Fecal incontinence is defined as accidental passing of solid or liquid stool or mucus from the rectum. Fecal incontinence includes the inability to hold a bowel movement until reaching a toilet as well as passing stool without being aware of it happening. Fecal incontinence markedly impedes social activities, employment, and daily activities, and 65% of SCI individuals require another person's assistance in cleaning up when an incontinence episode occurs. The condition affects over 15 million people in the US.

Since fecal incontinence involves passing of solid or liquid stool or mucus from the rectum, the solid or liquid stool or mucus must first be present in the rectum. To prevent fecal incontinence, the solid or liquid stool or mucus can be removed from the rectum by voluntary defecation or by use of a pharmacological agent that induces defecation.

Individuals with defecation dysfunction may also experience episodes of constipation, whereby individuals experience difficulty evacuating feces from the distal colon and rectum. Constipation is one of the most common forms of gastrointestinal hypomotility disorders and is one of the most common gastrointestinal complaints in the United States. Estimates of 1% to 8% of North Americans have chronic constipation. Self-treatment of constipation with over-the-counter (OTC) laxatives is by far the most common form of treatment. Over $1 billion is spent on laxative products each year in America.

Constipation is common in a number of gastrointestinal tract disorders including but not limited to irritable bowel syndrome, celiac disease or gluten-sensitive enteropathy, megacolon associated with hypothyroidism, pseudo-obstruction of the gastrointestinal tract, colitis, hypomotility of the colon associated with diabetes mellitus, adult onset Hirschsprung's disease, neurological disorders, myopathic disorders, spinal cord injury, Parkinson's disease, jejunal-ileal bypass with secondary megacolon, cancer chemotherapy, critical illness including severe burns and other major stresses, with syndromes of depression, the post-operative state, and other pathological conditions.

Present treatments for constipation include: over-the-counter (OTC) laxatives, AMITIZA (lubiprostone which is a chloride channel activator; approved for irritable bowel syndrome with constipation or IBS-C), and LINZESS (linaclotide; a guanylatecyclase-C agonist; approved for the treatment of IBS-C and chronic idiopathic cystitis, CIC). However, none of these available medications produce colon contraction and expulsion of feces; rather they increase the fluid in the intestines.

Capsaicin, or 8-methyl-N-vanillyl-6-nonenamide, is a naturally occurring chemical isolated from plants of the *Capsicum* genus (Fattori, Hohmann et al. 2016) and is an amide formed from condensation of vanillylamine and 8-methyl-6-nonenoyl-CoA (Reyes-Escogido Mde, Gonzalez-Mondragon et al. 2011). Capsaicin is one of the active ingredients in chili peppers, and capsaicin-induced activation of sensory afferent neuronal terminals is responsible for the sensations of heat, pain and discomfort experienced by an individual following ingestion of chili peppers (Fattori, Hohmann et al. 2016).

In the gastrointestinal tract, capsaicin receptors are abundantly expressed in nerve fibers of the distal colon and rectum of the mouse, where they mediate capsaicin-induced contractions of distal colon and rectum (Matsumoto, Kurosawa et al. 2009). Capsaicin has been used as a pharmacological tool to induce overactivity of the colon and initiate defecation when administered intracolonically, but not intrarectally, in conscious dogs (Hayashi, Shibata et al. 2010; Kikuchi, Shibata et al. 2014). In fact, the referenced publications teach away from rectal administration towards oral administration. In humans, activation of rectal afferent terminals by capsaicin to induce nociception was compared between healthy subjects and subjects having irritable bowel syndrome (IBS), with both groups reporting discomfort and "an urge to defecate", but not defecation, following intrarectal administration of capsaicin at concentrations of 0.01% and 0.1% (van Wanrooij, Wouters et al. 2014).

Intrarectal administration of capsaicin to induce defecation has not previously been demonstrated. Moreover, intrarectal administration of capsaicin to induce defecation in subjects having defecation dysfunction or in subjects having spinal cord injury has not been demonstrated. Intrarectal administration offers a safety advantage compared to oral drug administration because it concentrates exposure at the target tissue. As the desired therapeutic effects of intrarectal capsaicin are expulsion of the rectal contents and secretion of electrolytes, fluids, and mucus, it is expected that capsaicin will be rapidly eliminated from the rectum, terminating its actions and avoiding significant systemic absorption. Furthermore, rectal absorption of capsaicin may be less extensive than oral absorption.

No sensations of discomfort would be expected from intrarectal capsaicin administration in individuals with certain nervous system pathologies such as SCI due to disruption of spinal sensory pathways. Furthermore, it is possible that mild rectal discomfort would be preferable to the physical discomfort, stigma, time, and effort required for digital stimulation and manual extraction of stool currently experienced by some individuals with SCI.

Because existing therapies and treatments for defecation dysfunction are associated with limitations as described above, new therapies and treatments are therefore desirable. The presently disclosed subject matter provides such new therapies and treatments to address these limitations.

SUMMARY

In one embodiment of the presently disclosed subject matter, a method is provided for treating one of defecation dysfunction in a mammal in need of treatment, which comprises administering to the mammal a therapeutically effective amount of capsaicin or a pharmaceutically acceptable salt thereof, to induce the defecation. The therapeutically effective amount of capsaicin or pharmaceutically acceptable salt thereof may be administered on an as-needed basis.

In one embodiment of the presently disclosed subject matter, a method is provided for treating defecation dysfunction in a mammal in need of treatment, which comprises administering on an as-needed basis to the mammal a therapeutically effective amount of capsaicin (as represented by Formula I), or a pharmaceutically acceptable salt thereof, to induce the defecation.

Formula I

In one embodiment of the presently disclosed subject matter, a pharmaceutical formulation is provided for treating defecation dysfunction in a mammal in need of treatment on an as-needed basis, which comprises a therapeutically effective amount of capsaicin (FORMULA I), or a pharmaceutically acceptable salt thereof, and a carrier for administration of the capsaicin (FORMULA I) to the mammal on the as-needed basis.

In one embodiment of the presently disclosed subject matter, a packaged kit is provided for a patient to use in the treatment of loss of or decrease in voluntary control of defecation, comprising a pharmaceutical formulation of a therapeutically effective amount of capsaicin (FORMULA I), or a pharmaceutically acceptable salt thereof; a container housing the pharmaceutical formulation during storage and prior to administration; and instructions for carrying out administration in a manner effective to treat the loss or decrease in control of defecation.

In one embodiment of the presently disclosed subject matter, a packaged kit is provided for a patient to use for treating defecation dysfunction on an as-needed basis, comprising a pharmaceutical formulation of a therapeutically effective amount of capsaicin (FORMULA I), or a pharmaceutically acceptable salt thereof; a container housing the pharmaceutical formulation during storage and prior to administration; and instructions for carrying out administration on the as-needed basis to treat the defecation dysfunction.

In one embodiment of the presently disclosed subject matter, a method is provided for inducing defecation in a mammal, which comprises administering on an as-needed basis to the mammal a therapeutically effective amount of capsaicin (FORMULA I), or a pharmaceutically acceptable salt thereof, to induce defecation.

In one embodiment of the presently disclosed subject matter, a method is provided for treating fecal incontinence in a mammal, which comprises administering on an as-needed basis to the mammal a therapeutically effective amount of capsaicin (FORMULA I), or a pharmaceutically acceptable salt thereof, to induce defecation.

BRIEF DESCRIPTION OF THE FIGURES

The foregoing aspects and other features of the invention are explained in the following description, taken in connection with the accompanying drawings.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

In one embodiment of the presently disclosed subject matter, a method is provided for treating defecation dysfunction in a mammal in need of treatment, which comprises administering on an as-needed basis to the mammal a therapeutically effective amount of capsaicin (FORMULA I), or a pharmaceutically acceptable salt thereof, to induce defecation. Thus, the compositions and methods of the present disclosure meet an existing need for new treatments for defecation dysfunction including, for example, constipation and the inability to voluntarily defecate. The defecation dysfunction can be a result of a wide range of injuries, conditions, diseases, or disorders, including one or more of spinal cord injury, traumatic brain injury, multiple sclerosis, spina bifida, degenerative brain disease, Alzheimer's, Parkinson's, dementia, diabetes, advanced age, and postoperative status.

In another embodiment of the presently disclosed subject matter, a method is provided for inducing defecation in a mammal, which comprises administering on an as-needed basis to the mammal a therapeutically effective amount of capsaicin (FORMULA I), or a pharmaceutically acceptable salt thereof, to induce defecation. Thus, the compositions and methods of the present disclosure meet an existing need for new treatments to induce defecation in persons who are, for example, unconscious to cause the defecation before the person defecates unconsciously. Another advantage of the methods and compositions of the present disclosure is for a pet owner who may want to induce defecation in their normal dog, for example, at a specific, convenient location or time.

To provide an effective treatment for anal sphincter dyssynergia, the administering of capsaicin according to the methods and formulations of the present disclosure may be combined with one or more sphincter relaxants such as, but not limited to, alpha adrenergic receptor blockers, nitric oxide (NO) donors, PDE5 inhibitors, and prostaglandin E receptor (EP1,2,3) agonists.

A therapeutically effective amount of an active agent of the presently disclosed subject matter may be administered via intrarectal administration.

Methods are provided herein for using an active agent or otherwise referred to herein interchangeably as a "pharmaceutical agent" to provide drug-induced defecation. The drug-induced defecation can be useful for those with defecation dysfunction or for a mammal for which inducing defecation is otherwise desirable. The pharmaceutical agent of the present disclosure can include capsaicin. The compositions and methods of the present disclosure provide pharmaceutical formulations and methods of administration of capsaicin to provide a duration of action which can produce defecation and then allow the rectum to subsequently relax to allow for storage of newly-formed stool to prevent subsequent incontinence. The formulations and methods of administration of the present disclosure can minimize the duration of side-effects in other organs systems.

One advantage of the presently described subject matter is provision of capsaicin that can be administered such that it affects a rapid-onset and short duration of action for administration to mammals to achieve a rapid-onset and short duration contraction of the rectum. Surprisingly, the contractions produced by administration of capsaicin can actually elicit physiologically significant contraction of the rectum and defecation. For example, capsaicin-induced contraction in the rectum would have been expected to cause contraction and closure of the anal sphincter and presumably prevention of defecation.

Another advantage of the presently described method of administration is that the capsaicin-induced defecation can be achieved without the adverse effect of oral burning sensations and contractions of the entire GI tract to produce painful cramps.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

By "SCI" is meant spinal cord injury.

By "capsaicin" (FORMULA I) is meant 8-methyl-N-vanillyl-6-nonenamide.

FORMULA I

By an "effective" amount or a "therapeutically effective amount" of a drug or pharmacologically active agent of the present disclosure including, for example, capsaicin, or a pharmaceutically acceptable salt thereof, is meant a non-toxic but sufficient amount of the drug or active agent to provide the desired effect, i.e., treating defecation dysfunction such as effectuating voluntary defecation and/or relieving fecal incontinence. It is recognized that the effective amount of a drug or pharmacologically active agent will vary depending on the route of administration, the selected compound, and the species to which the drug or pharmacologically active agent is administered. It is also recognized that one of skill in the art will determine appropriate effective amounts by taking into account such factors as metabolism, bioavailability, and other factors that affect levels of a drug or pharmacologically active agent following administration within the unit dose ranges disclosed further herein for different routes of administration.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt or an analog) of an active agent, it is to be understood that the compound is pharmacologically active as well, i.e., therapeutically effective for treating defecation dysfunction.

By "continuous" dosing is meant the chronic or uninterrupted administration of a selected active agent. For example, continuous dosing can include daily dosing.

By "as-needed" dosing, also known as "pro re nata" or "prn" dosing, and "on demand" dosing or administration is meant the administration of a single dose of the active agent at some time prior to commencement of defecation. Administration can be immediately prior to such a time, including about 0 minutes, about 0 to about 5 minutes, about 0 to about 10 minutes, about 0 to about 20 minutes, about 0 to about 30 minutes, or about 0 to about 40 minutes, prior to such a time, depending on the formulation and the route of administration.

By "rapid-onset" is intended any period of time up to and including a $T_{max}$ between about 0 sec to about 1 hour, between about 0 sec to about 45 minutes, between about 0 sec to about 30 minutes, between about 0 sec to about 15 minutes, or between about 0 sec to about 10 minutes, or between 0 sec to 5 min, after active agent administration.

In the methods and compositions described herein, the rapid onset of capsaicin can be characterized by an onset of action ranging from about 0 sec to about 1 hour after capsaicin administration, from about 0 sec to about 45 minutes after capsaicin administration, from about 0 sec to about 30 minutes after capsaicin administration, from about 0 sec to about 15 minutes after capsaicin administration, from about 0 sec to about 10 minutes after capsaicin administration, or from about 0 sec to about 5 min after capsaicin administration.

By "short duration of action" is intended a duration of action between about 2 hours to about 10 minutes, between about 1 hour to about 10 minutes, and between about 30 minutes to about 10 minutes, and between 15 to about 5 minutes after active agent administration.

In the methods and compositions described herein, the short duration of action of capsaicin can be characterized by a duration of action ranging from about 1 hour to about 10 minutes after capsaicin administration, from about 30 minutes to about 10 minutes after capsaicin administration, or from about 15 to about 5 minutes after capsaicin administration.

The term "delayed release" is used in its conventional sense to refer to a drug formulation that provides for an initial release of the drug after some delay following drug administration and that preferably, although not necessarily, includes a delay of up to about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

The term "immediate release" is used in its conventional sense to refer to a drug formulation that provides for release of the drug immediately after drug administration.

Capsaicin, or the pharmaceutically acceptable salt thereof, can be formulated as an immediate release dosage form. As-need administering can range from about 0 minutes to about 40 minutes prior to when the defecation is desired, from about 0 minutes to about 20 minutes prior to when the defecation is desired, or from about 0 minutes to about 5 minutes prior to when the defecation is desired.

The term "defecation dysfunction" refers to the inability to expel feces from the distal bowel and rectum. Defecation dysfunction is also known as defecation disorder, anorectal evacuation disorder, fecal impaction, constipation, or colonic dysmotility.

By the term "parenteral" drug delivery is meant delivery without first having to pass through the alimentary canal, or digestive tract. Parenteral drug delivery may be "transmucosal," referring to administration of a drug to the mucosal surface of a mammal so that the drug passes through the mucosal tissue. Transmucosal drug delivery may be "rectal" or "transrectal" or "intrarectal" drug delivery, referring to delivery of a drug by passage of a drug into or through a mammal's rectal mucosa.

In one embodiment, the presently disclosed subject matter provides a strategy for administering compositions and formulations of capsaicin, when convenient and appropriate for a person suffering from a defecation dysfunction or otherwise in need of such treatment such as, for example, a person who is unconscious and may defecate unconsciously. The compositions and methods of the present disclosure may also be useful to allow a pet owner to induce defecation in their pet at a specific, convenient location or time.

In one embodiment of the present disclosure, a method is provided for treating defecation dysfunction in a mammal in need of treatment. In another embodiment of the present disclosure, a method is provided for inducing defecation in a mammal that may not necessarily have a defecation dysfunction. The methods include administering to the mammal a therapeutically effective amount of capsaicin or a pharmaceutically acceptable salt thereof. The mammal can include but is not limited to, for example, a human, a cat, or a dog.

Formulations of the compositions and active agents of the present disclosure are provided in dosage forms, which can include rapid-onset, and short duration forms, so long as they are formulated to achieve administration of an active agent, as described further herein.

In one embodiment, one or more additional active agents can be administered either simultaneously or sequentially with capsaicin in either a separate or a single formulation. The additional active agent may be one that is effective in treating bowel dysfunction that accompanies fecal retention. The additional active agent may be one that potentiates the effect of capsaicin for treating defecation dysfunction. Suitable additional active agents include, but are not limited to, for example, alpha adrenergic antagonists (e.g. silodosin, terazosin, tamsulosin, doxazosin, prazosin, alfuzosin), phosphodiesterase inhibitors (e.g. sildenafil, vardenafil, tadalafil) lubiprostone, linaclotide, and/or any agent that does not inhibit the action of the primary active agent.

The additional active agent may be a compound that can induce one of colon contraction and/or sphincter relaxation in the subject. The anal sphincter relaxant agent can be, for example, one of vasoactive intestinal polypeptide (VIP), a NO donor, amyl nitrate, butyl nitrate, glyceryltrinitrate, an alpha-adrenergic receptor blocker, tamsulosin, silodosin, alfuzosin, naftopidil, or other suitable anal sphincter relaxant agents.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by a metabolic system.

Other salts, enantiomers, analogs, esters, amides, prodrugs, active metabolites, and derivatives of the active agents may be prepared using standard techniques known to those skilled in the art of synthetic organic chemistry or may be deduced by reference to the pertinent literature. In addition, chiral active agents may be in isomerically pure form, or they may be administered as a racemic mixture of isomers.

The active agents of the present disclosure can be administered by a mode including transmucosal or transrectal administration.

The active agents of the present disclosure can be contained within a pharmaceutical formulation. The pharmaceutical formulation can be a unit dosage form. The pharmaceutical formulation dosage form can be selected from the group consisting of suppositories, capsules, tablets, powders, creams, ointments, gels, foams, solutions, emulsions, and suspensions. The pharmaceutical formulation can include a permeation enhancer.

The dosage form may be rectally administered. Further, those of ordinary skill in the art can readily deduce suitable formulations involving these compositions and dosage forms, including those formulations as described elsewhere herein.

The dosage form may be a tablet. Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), tablets can generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of *theobroma*, glycerin, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition and must be suitable for intrarectal insertion.

The dosage form may also be a capsule, comprising a hard or soft capsule containing a fill consisting of one or more inert ingredients, and one or more coatings on the capsule, wherein at least one coating comprises a suitable formulation and dosage form.

Preferred transrectal dosage forms include rectal suppositories, capsules, tablets, powders, creams, ointments, gels, foams, solutions, emulsions, and suspensions (Jannin, Lemagnen et al. 2014). The suppository, capsule, tablet, powder, cream, ointment, gel, foam, solution, emulsion, or suspension formulation for transrectal delivery comprises a therapeutically effective amount of the selected active ingredient and one or more conventional nontoxic carriers suitable for transrectal drug administration. The transrectal dosage forms of the present invention can be manufactured using conventional processes. The transrectal dosage form can be fabricated to disintegrate rapidly or over a period of several hours. The time period for complete disintegration is preferably in the range of from about 1 minute to about 6 hours, and optimally is less than about 3 hours.

For transrectal administration, the formulation may comprise a rectal dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Transrectal drug administration can be carried out in a number of different ways using a variety of rectal dosage forms. For example, the drug can be introduced into the rectum from a flexible tube, squeeze bottle, or pump. The drug may also be contained in coatings, pellets, tablets, capsules or suppositories that are absorbed, melted or bio-eroded in the rectum. In certain embodiments, the drug is included in a coating on the exterior surface of a rectal insert. It is preferred, although not essential, that the drug be delivered from at least about 1 cm into the rectum, and preferably from at least about 4 cm into the rectum. Generally, delivery from at least about 3 cm to about 8 cm into the rectum will provide effective results in conjunction with the present method.

Rectal suppository formulations containing PEG or a PEG derivative may be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of rectal suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that rectal suppositories contain one or more solubilizing agents effective to increase the solubility of the active agent in the PEG or other transrectal vehicle.

The rectal dosage form will preferably comprise a suppository that is on the order of from about 0.1 to about 10 cm in length, preferably from about 0.5 to about 3 cm in length, and less than about 2 cm in width, preferably less than about 1 cm in width. The weight of the suppository will typically be in the range of from about 0.5 gm to about 5 gm, preferably in the range of from about 1 gm to about 2 gm. However, it will be appreciated by those skilled in the art that the size of the suppository can and will vary, depending on the potency of the drug, the nature of the formulation, and other factors. Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glycerylmonostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the CARBOPOL trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the transrectal formulations. For example, solubilizers may be used to solubilize certain active agents. For those drugs having an unusually low rate of permeation through the mucosal tissue, it may be desirable to include a permeation enhancer in the formulation. Examples of suitable transrectal permeation enhancers include dimethyl sulfoxide ("DMSO"), dimethyl formamide ("DMF"), N, N-dimethylacetamide ("DMA"), decyl methyl sulfoxide ("C10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark AZONE from Nelson Research & Development Co., Irvine, Calif.), SEPA (available from Macrochem Co., Lexington, Mass.), surfactants as discussed above, including, for example, TERGITOL, NONOXYNOL-9 and TWEEN-80, and lower alkanols such as ethanol.

One of skill in the art recognizes that the concentration of the active agent in any of the aforementioned dosage forms and compositions can vary a great deal and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration. Similarly, the affinity of capsaicin for the capsaicin receptor is expected to influence the effective doses and concentrations of capsaicin.

For capsaicin, the unit dose for transmucosal administration can be in the range of from about 1 ng to about 10,000 mg, in the range of from about 100 ng to about 5,000 mg. The unit dose for transmucosal administration can be greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg, about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. One of ordinary skill in the art of pharmaceutical formulation can also readily deduce suitable unit doses for other types of active agents that may be incorporated into a dosage form of the invention.

A therapeutically effective amount of a particular active agent administered to a given mammal will, of course, be dependent on a number of factors, including the concentration of the specific active agent, composition or dosage form, the selected mode of administration, the age and general condition of the mammal being treated, the severity of the mammal's condition, and other factors known to the prescribing physician. However, one of skill in the art would readily recognize that the therapeutically effective amount of a particular active agent must be selected so as to allow for as-needed administration, as defined further herein.

With an immediate release dosage form, as-needed administration may involve drug administration immediately prior to when commencement of defecation would be desirable. The as-need administration can range from about 0 minutes to about 40 minutes prior to the desired emptying, from about 0 minutes to about 20 minutes prior, or about 0 minutes to about 5 minutes prior.

In another embodiment, a packaged kit is provided that contains the pharmaceutical formulation to be administered, i.e., a pharmaceutical formulation containing a therapeutically effective amount of a selected active agent for the treatment of defecation dysfunction, a container, preferably sealed, for housing the formulation during storage and prior to use, and instructions for carrying out drug administration in a manner effective to treat the defecation dysfunction. The instructions will typically be written instructions on a package insert and/or on a label. Depending on the type of formulation and the intended mode of administration, the kit may also include a device for administering the formulation. The formulation may be any suitable formulation as described herein. The active agent can be capsaicin (FORMULA I), or a pharmaceutically acceptable salt thereof. The manner for treating the defecation dysfunction may be administration on an as-needed basis to treat the defecation dysfunction. The as-needed basis can range from about 0 minutes to about 40 minutes prior to when the defecation is desired, from about 0 minutes to about 20 minutes prior to when the defecation is desired, or from about 0 minutes to about 5 minutes prior to when defecation is desired.

The kit may contain multiple formulations of different dosages of the same agent. The kit may also contain multiple formulations of different active agents. The kit may contain formulations suitable for sequential, separate and/or simultaneous use in the treatment of defecation dysfunction, and instructions for carrying out drug administration where the formulations are administered sequentially, separately and/or simultaneously in the treatment of defecation dysfunction. The parts of the kit may be independently held in one or more containers—such as bottles, syringes, plates, wells, blister packs, or any other type of pharmaceutical packaging.

In another embodiment, a pharmaceutical formulation is provided for treating defecation dysfunction in a mammal in need of treatment on an as-needed basis, which includes a therapeutically effective amount of capsaicin, or a pharmaceutically acceptable salt thereof, and a carrier for administration of capsaicin to the mammal on the as-needed basis. The pharmaceutical formulation can also be useful for inducing defecation in a mammal without an actual defecation dysfunction. The carrier for administration may be any suitable formulation as described herein. The as-need administration can range from about 0 minutes to about 40 minutes prior to when the defecation is desired, from about 0 minutes to about 20 minutes prior to when the defecation is desired, or from about 0 minutes to about 5 minutes prior to when the defecation is desired.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods: Measurement of Capsaicin-Induced Rectal Responses

The following methods were used to determine the efficacy, specificity, onset of action and the duration of action of capsaicin to induce defecation in naïve rats and a rat model of chronic spinal cord injury. In addition, the reproducibility of multiple dosing and the pharmacodynamic (PD) responses of administering capsaicin via intrarectal administration were explored.

General: In vivo studies were performed in anesthetized, acute spinal cord injured (SCI) rats, anesthetized spinal intact rats, and awake chronic spinal cord injured rats. Adult female and male Sprague Dawley rats (Charles River, N.C.; 250-650 g) were housed at an AAALAC approved facility in cages (1-3/cage) with free access to water and food in a colony room that was maintained on a 12 hr/12 hr light/dark cycle.

For chronic SCI model preparation, animals were anesthetized with a mixture of ketamine/xylazine (50-100 mg/kg and 5-10 mg/kg intraperitoneal, respectively), the skin and muscle on the dorsal side at the level of the thoracic vertebrae were incised, and the spinal cord was carefully exposed by a laminectomy and transected at either T3-T4 or T8-T10 spinal level. Gelfoam® was placed at the incision site and the muscle and skin overlying the vertebrae were closed with wound clips. The animal recovered from surgery for 7-10 weeks before being studied.

For the acute SCI model, animals were anesthetized with urethane (1.0-1.4 g/kg subcutaneous injection), the skin and muscle on the dorsal side at the level of the thoracic vertebrae were incised, and the spinal cord was carefully exposed by a laminectomy and transected at T8-T10 spinal level. Gelfoam® was placed at the incision site and the muscle and skin overlying the vertebrae were closed with wound clips. The spinal cord was transected at least 60 min before starting the experimental protocol.

For all rectal contractility studies, animals were anesthetized with urethane (1.0-1.4 g/kg subcutaneous injection). Surgical procedures were then performed with the addition of isoflurane anesthesia (0.05-1.5% in O2) as needed. Rectal pressure signals were amplified and displayed on a computer using LABCHART (AD Instruments, Colorado Springs, Colo.).

Rectal Contractility: Rectal pressures were measured via a latex balloon catheter (length 1.5-4 cm) inserted (~4 cm) into the distal rectal region. The catheter was connected to a pressure monitoring system. The pressure in the balloon catheter was slowly increased to 15-20 mmHg by infusing saline (0.2-0.5 ml total volume) and this pressure was maintained throughout the study, allowing drug-induced changes in rectal pressure to be monitored. Parameters measured included peak rectal pressure response, duration of time above baseline activity (in the $1^{st}$ 5 min after drug administration), area under the curve (measured during the $1^{st}$ 5 min after drug administration) and the number of contractile events after vehicle and drug administration.

Defecation in awake animals was monitored in metabolism cages. Animals were habituated to handling and the metabolism cages on 2-4 occasions prior to dosing and were then randomized to a treatment arm. Rats were weighed and placed into metabolism cages for 10 min prior to intrarectal administration of vehicle or capsaicin. The number of fecal pellets and timing of events were recorded by trained personnel that were blinded to treatment. Fecal weight is weighed at 10 and 30 min post dosing. Animals were re-tested 2-3 days later in a cross over design.

Dosing: Intrarectal capsaicin was administered in a dose range of 0.1-2% wt/vol. Capsaicin was dissolved in 95% ethanol at 50-100 mg/mL and then diluted to 2-20 mg/mL with either saline or water to form a suspension and administered intrarectally as a solution using a micropipette, blunt tip tube (22 G) or as a small solution-soaked cotton ball (3-5 mm diameter). Vehicle doses were prepared using the same concentrations of ethanol in water or saline.

Data analysis: Data were examined qualitatively and quantitatively. The mean, standard deviation and standard error of the mean were calculated using MICROSOFT EXCEL. One way ANOVA tests were performed with PRISM 5 for WINDOWS (GraphPad Software, Inc., La Jolla, Calif.) and unpaired and paired t-tests were performed in EXCEL. P<0.05 is considered statistically significant.

Example 2

Intrarectal Capsaicin Solution Produced Transient, Repeatable Increased Rectal Pressure Responses in Anesthetized Naïve Rats Methods: Capsaicin was administered to anesthetized spinal intact male and female rats (N=4 males and 1 female)

instrumented for rectal pressure recording via a balloon catheter inserted into the rectum 2-4 cm from the anus. Capsaicin was administered as 0.2% solution (0.05-0.32 mL of a 2 mg/ml solution in 4.7 or 9.5% ethanol/saline) via a PE50 tube that was inserted into the rectum alongside the balloon catheter. For comparison, vehicle was administered to all rats using the same techniques.

Figure 2:
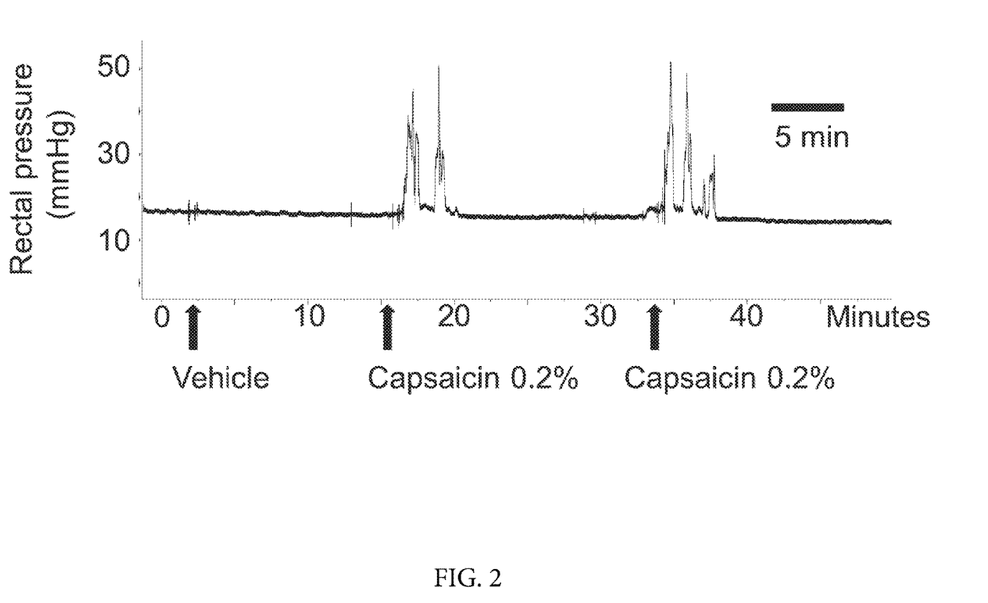
FIG. 2 shows that intrarectal capsaicin produced a transient, repeatable increase in rectal pressure.

Results: Intrarectal administration of 0.2% capsaicin solution produced a transient rectal pressure increase in 5 of 5 rats with a rapid-onset time of 1-2 min and short duration (5 min). Vehicle did not evoke any rectal activity. FIG. 2 shows a representative example of rectal pressure measured from a male rat. Repeat dosing of 0.2% capsaicin 20 min after the initial dose evoked a similar response (FIG. 2). Administration of vehicle or capsaicin solution is indicated by arrows in FIG. 2. As illustrated by FIG. 2, intrarectal capsaicin produced a transient, repeatable increase in rectal pressure.

Conclusions: Intrarectal capsaicin, but not vehicle, produced a transient increase in rectal pressure that demonstrated a rapid-onset and short duration. The increase in rectal pressure was repeatable in the same animal.

Example 3

Intrarectal Capsaicin Solution Produced an Increase in Rectal Pressure and Expulsion of Rectal Contents in Anesthetized Naïve Rats Methods: Capsaicin was administered to an anesthetized spinal intact male rat instrumented for rectal pressure recording via a balloon catheter inserted into the rectum 2-4 cm from the anus. Capsaicin was administered as 0.2% solution (0.2%, 0.25 mL) in ethanol/saline via a PE50 tube that was inserted into the rectum alongside the balloon catheter. Vehicle was administered to all rats using the same techniques. Administration of capsaicin solution is indicated by filled arrow in FIG. 3.

Figure 3:
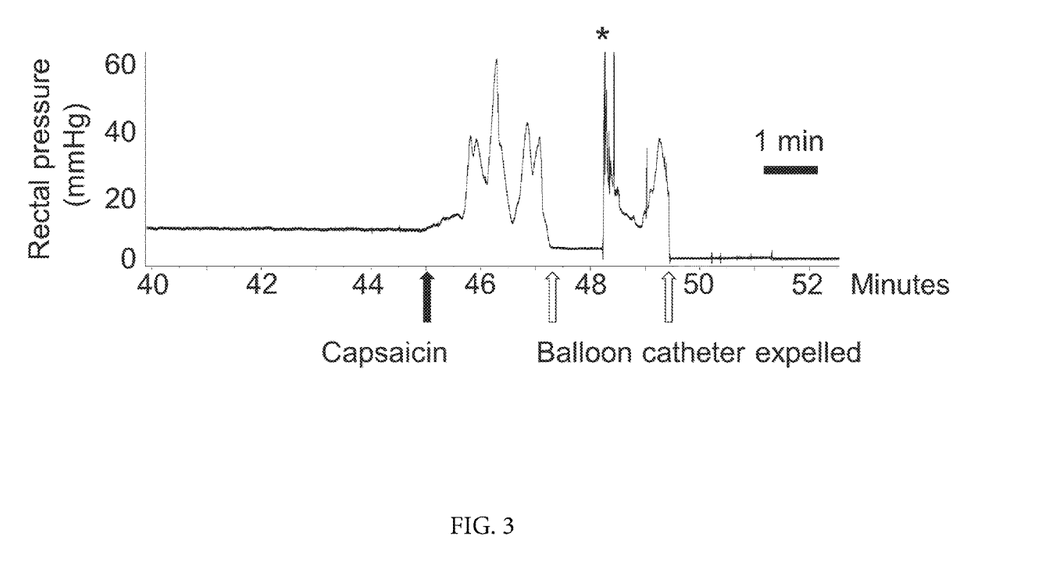
FIG. 3 shows that capsaicin-induced rectal pressure responses are capable of expelling rectal contents.

Results: Capsaicin produced a rapid-onset increase in rectal pressure within 1 minute of dosing. The rectal balloon catheter was expelled from the rectum through the anus due to the capsaicin-induced increase in rectal pressure (FIG. 3). The rectal response sufficient to expel the balloon catheter is indicated by open arrows in FIG. 3. The balloon catheter was re-inserted after the initial expulsion (*) but was expelled again.

Conclusions: Intrarectal capsaicin produced a rapid-onset increased rectal pressure of sufficient intensity to expel rectal contents.

Example 4

Intrarectal Insertion of a Cotton Ball Containing Capsaicin Produced Transient, Increased Rectal Pressure Responses in Anesthetized, Spinal Cord Injured (SCI) Rats Methods: Capsaicin was administered to 2 anesthetized acute T9-transected SCI female rats instrumented for rectal pressure recording via a balloon catheter inserted into the rectum 2-4 cm from the anus. To increase the contact time of the capsaicin solution, capsaicin (0.2%) was administered via a fluid-soaked cotton ball. A small cotton ball soaked in capsaicin (50 uL of a 0.2% solution) was administered into the rectum (filled arrows in FIG. 4). The cotton ball was placed into the anal canal at the distal rectum. The cotton ball was removed 5-12 min later (asterisks in FIG. 4). Top and bottom traces in FIG. 4 were recorded from separate rats.

Figure 4:
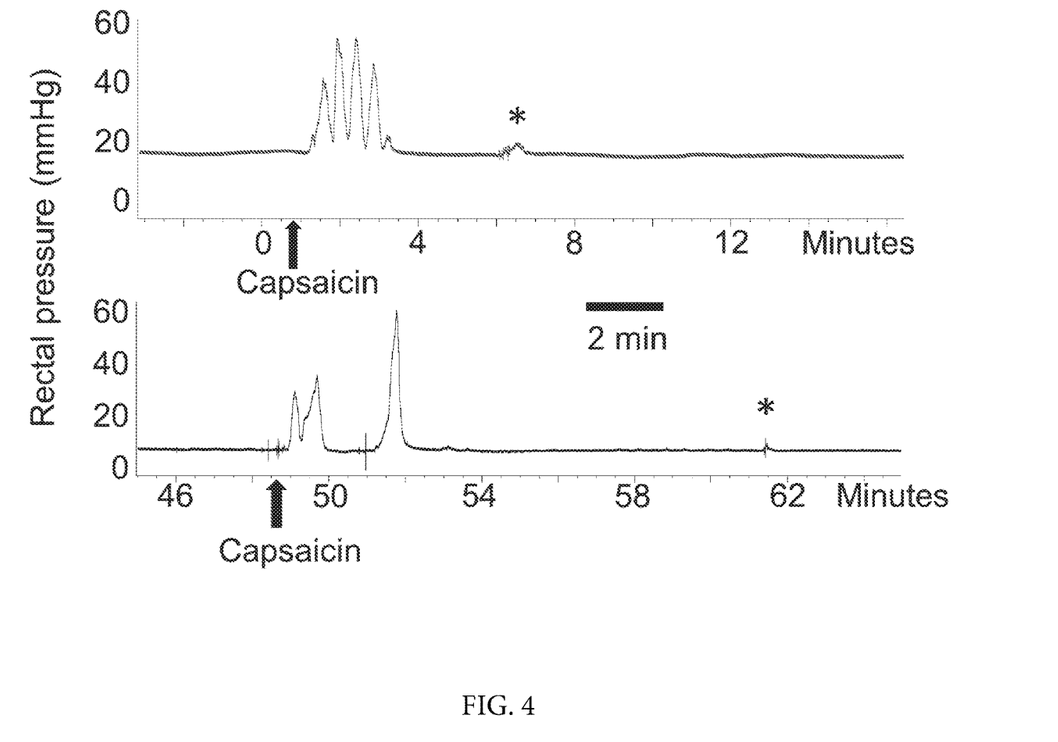
FIG. 4 shows that intrarectal administration of a capsaicin-soaked cotton ball produced rectal pressure responses similar to those produced by intrarectal capsaicin solution dosing.

Results: A rapid-onset (<2 min) and short duration (<5 min) capsaicin-induced rectal pressure increase was observed in both rats. FIG. 4 shows a representative example of rectal pressure measured from the 2 female rats. As shown, intrarectal administration of a capsaicin-soaked cotton ball produced rectal pressure responses similar to those produced by intrarectal administration of capsaicin solution. Placement of vehicle-soaked cotton ball produced either no response or a small increase in rectal activity, due to manual insertion of the cotton ball.

Conclusions: Capsaicin produced an increase in rectal pressure in spinal injured rats when administered using a locally restricted dosage form.

Example 5

Intrarectal Capsaicin Produced Defecation in Conscious Spinal Injured Rats

Methods: Defecation in rats was monitored in metabolism cages. Chronic spinal cord injured (cSCI) rats were habituated to handling and the metabolism cages on 2-4 occasions before dosing, then randomized to the treatment arm. Rats were weighed and placed into metabolism cages for 10 min prior to receiving an intrarectal dose of vehicle or capsaicin. Since manual stimulation during intrarectal dosing in conscious rats can induce defecation, the tip of a small cotton swab was inserted into the anus prior to dose administration, to stimulate natural defecation of any fecal pellets that were located in the region of the anal sphincter. This manipulation resulted in defecation of 1-3 fecal pellets that were near expulsion with concomitant contractions/relaxation of the anal sphincter. Once the anal sphincter had ceased contracting/relaxing (15-90 s) a fine catheter (22 G soft/flexible blunt tip catheter) was used to dose the vehicle or capsaicin, as this method produced little manual stimulation. Capsaicin was prepared as a 0.2 or 2% solution (2 or 20 mg/ml in diluted ethanol/water; vehicle corresponding to each dose concentration was 1.9 and 19% ethanol/water, respectively). Dose volumes were 0.1 mL and administered via the catheter inserted ~1 inch through the anus into the rectum. The number of fecal pellets and timing of events were recorded by trained personnel blinded to the treatment. Fecal weight was recorded at 10 and 30 min post dosing. Animals were re-tested 2-3 days later in a cross over design.

Results: Capsaicin significantly increased the number and total weight of fecal pellets expelled compared to vehicle (Table 1). Defecation occurred within 5 min and was complete within 10 min. No defecation was observed between 10-30 min post-dosing in any group.

Conclusions: Capsaicin induced a significant increase in defecation in conscious chronic spinal cord injured rats.

TABLE 1

Responses to intrarectal dosing in conscious cSCI rats

|  | Vehicle 1.9% | Vehicle 19% | Capsaicin 0.2% | Capsaicin 2% |
|---|---|---|---|---|
| Number of fecal pellets | 0.83 + 0.45 | 0.67 + 0.14 | 2.17 + 0.84 [+] | 2.00 + 0.68 [+] |

TABLE 1-continued

Responses to intrarectal dosing in conscious cSCI rats

|  | Vehicle 1.9% | Vehicle 19% | Capsaicin 0.2% | Capsaicin 2% |
|---|---|---|---|---|
| Total fecal weight (g) | 0.983 + 0.701 | 0.816 + 0.206 | 1.169 + 0.0489 | 1.265 + 0.414 * |

Data represent the number and weight of fecal pellets produced within 10 min of dosing.
N = 6 per group, values are mean + SD.
* indicates significant difference compared to 19% vehicle (p < 0.05 level, unpaired t-test p = 0.016527).
† indicates significant increase in number of fecal pellets (p < 0.1 level, 1.9% vehicle vs 0.2% capsaicin, p = 0.05822; 19% vehicle vs 2% capsaicin, p = 0.055235).

One skilled in the art will readily appreciate that the presently described subject matter is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference.

Callaghan, B., J. B. Furness and R. V. Pustovit (2018). "Neural pathways for colorectal control, relevance to spinal cord injury and treatment: a narrative review." *Spinal Cord* 56(3): 199-205.

National Spinal Cord Injury Statistical Center, Facts and Figures at a Glance. Birmingham, Ala.: University of Alabama at Birmingham, 2019.

Fattori, V., M. S. Hohmann, A. C. Rossaneis, F. A. Pinho-Ribeiro and W. A. Verri (2016). "Capsaicin: Current Understanding of Its Mechanisms and Therapy of Pain and Other Pre-Clinical and Clinical Uses." *Molecules* 21(7).

Hayashi, K., C. Shibata, M. Nagao, M. Sato, M. Kakyo, M. Kinouchi, F. Saijo, K. Miura, H. Ogawa and I. Sasaki (2010). "Intracolonic capsaicin stimulates colonic motility and defecation in conscious dogs." *Surgery* 147(6): 789-797.

Jannin, V., G. Lemagnen, P. Gueroult, D. Larrouture and C. Tuleu (2014). "Rectal route in the 21st Century to treat children." *Adv Drug Deliv Rev* 73: 34-49.

Kikuchi, D., C. Shibata, H. Imoto, S. Someya, T. Miyachi, K. Miura, T. Naitoh and M. Unno (2014). "Role of the intraluminal contents and the continuity of intrinsic neurons in intracolonic capsaicin-induced contraction and defecation in dogs." *Surg Today* 44(1): 152-159.

MacDonagh, R., W. M. Sun, D. G. Thomas, R. Smallwood and N. W. Read (1992). "Anorectal function in patients with complete supraconal spinal cord lesions." *Gut* 33(11): 1532-1538.

Matsumoto, K., E. Kurosawa, H. Terui, T. Hosoya, K. Tashima, T. Murayama, J. V. Priestley and S. Horie (2009). "Localization of TRPV1 and contractile effect of capsaicin in mouse large intestine: high abundance and sensitivity in rectum and distal colon." *Am J Physiol Gastrointest Liver Physiol* 297(2): G348-360.

Reyes-Escogido Mde, L., E. G. Gonzalez-Mondragon and E. Vazquez-Tzompantzi (2011). "Chemical and pharmacological aspects of capsaicin." *Molecules* 16(2): 1253-1270.

Shafik, A. (1996). "Recto-colic reflex: role in the defecation mechanism." *Int Surg* 81(3): 292-294.

Shafik, A. (1999). "A study of the effect of distension of the rectosigmoid junction on the rectum and anal canal with evidence of a rectosigmoid-rectal reflex." *J Surg Res* 82(1): 73-77.

Shafik, A., O. El-Sibai and I. Ahmed (2001). "Role of the sigmoid colon in the defecation mechanism with evidence of sigmoido-anal inhibitory and ano-sigmoid excitatory reflex." *Front Biosci* 6: B25-29.

van Wanrooij, S. J., M. M. Wouters, L. Van Oudenhove, W. Vanbrabant, S. Mondelaers, P. Kollmann, F. Kreutz, M. Schemann and G. E. Boeckxstaens (2014). "Sensitivity testing in irritable bowel syndrome with rectal capsaicin stimulations: role of TRPV1 upregulation and sensitization in visceral hypersensitivity?" *Am J Gastroenterol* 109(1): 99-109.

That which is claimed:

1. A method for inducing defecation in a mammal, comprising administering to the mammal a therapeutically effective amount of capsaicin or a pharmaceutically acceptable salt thereof as an active agent for inducing defecation, wherein the administering is rectal and capsaicin is the only active agent administered for inducing defecation.

2. The method of claim 1, wherein the therapeutically effective amount of capsaicin or the pharmaceutically acceptable salt thereof is administered on an as-needed basis.

3. The method of claim 1, wherein the rectal administering is selected from the group consisting of one or more of rectal suppositories, capsules, tablets, powders, creams, ointments, gels, foams, solutions, emulsions, and suspensions.

4. The method of claim 1, wherein the mammal is a human, a cat, or a dog.

5. The method of claim 1, wherein administering ranges from about 0 minutes to about 30 minutes prior to when the defecation is desired.

6. The method of claim 5, wherein administering ranges from about 0 minutes to about 10 minutes prior to when the defecation is desired.

7. A method for treating defecation dysfunction in a mammal in need of treatment, comprising administering to the mammal a therapeutically effective amount of capsaicin or a pharmaceutically acceptable salt thereof as an active agent for treating defecation dysfunction, wherein the administering is rectal and capsaicin is the only active agent administered for treating defecation dysfunction.

8. The method of claim 7, wherein the therapeutically effective amount of capsaicin or the pharmaceutically acceptable salt thereof is administered on an as-needed basis.

9. The method of claim 7, wherein the defecation dysfunction is a result of one or more of spinal cord injury, traumatic brain injury, multiple sclerosis, spina bifida, degenerative brain disease, Alzheimer's, Parkinson's, dementia, diabetes, advanced age, idiopathic constipation or postoperative status.

10. The method of claim 7, wherein the defecation dysfunction is a result of fecal incontinence.

11. The method of claim 7, wherein the rectal administering comprises a rectal suppository.

12. The method of claim 7, wherein the mammal is a human, a cat, or a dog.

13. The method of claim 7, wherein administering ranges from about 0 minutes to about 30 minutes prior to when the defecation is desired.

14. The method of claim 13, wherein administering ranges from about 0 minutes to about 10 minutes prior to when the defecation is desired.

15. A method for treating fecal incontinence in a mammal in need of treatment, which comprises administering to the mammal a therapeutically effective amount of capsaicin or a pharmaceutically acceptable salt thereof as an active agent for treating fecal incontinence by inducing voluntary defecation, wherein the administering is rectal and capsaicin is the only active agent administered for treating fecal incontinence, to induce the as-needed voluntary defecation.

16. The method of claim 15, wherein the therapeutically effective amount of capsaicin or the pharmaceutically acceptable salt thereof is administered on an as-needed basis.

* * * * *